(12) United States Patent
Kaplan

(10) Patent No.: US 11,113,985 B2
(45) Date of Patent: Sep. 7, 2021

(54) VISUAL ACUITY MEASUREMENT APPARATUS

(71) Applicant: Focus Reading Technology Inc., Armonk, NY (US)

(72) Inventor: Howard Jay Kaplan, Armonk, NY (US)

(73) Assignee: Focus Reading Technology Inc., Armonk, NY (US)

( * ) Notice: Subject to any disclaimer, the term of this patent is extended or adjusted under 35 U.S.C. 154(b) by 377 days.

(21) Appl. No.: 16/117,122

(22) Filed: Aug. 30, 2018

(65) Prior Publication Data

US 2019/0066531 A1 Feb. 28, 2019

Related U.S. Application Data

(60) Provisional application No. 62/552,055, filed on Aug. 30, 2017.

(51) Int. Cl.
| | |
|---|---|
| *G09B 17/00* | (2006.01) |
| *G06F 3/01* | (2006.01) |
| *A61B 3/032* | (2006.01) |
| *A61B 3/02* | (2006.01) |
| *A61B 3/00* | (2006.01) |
| *G10L 15/26* | (2006.01) |

(52) U.S. Cl.
CPC .............. *G09B 17/003* (2013.01); *A61B 3/00* (2013.01); *A61B 3/022* (2013.01); *A61B 3/032* (2013.01); *G06F 3/013* (2013.01); *G10L 15/26* (2013.01)

(58) Field of Classification Search
CPC ...... G09B 17/00; G09B 17/003; G09B 17/02; G09B 17/04
See application file for complete search history.

(56) References Cited

U.S. PATENT DOCUMENTS

| | | | | |
|---|---|---|---|---|
| 6,154,757 A | * | 11/2000 | Krause | G06F 40/166 715/205 |
| 7,367,807 B1 | * | 5/2008 | Pennebaker | G09B 5/00 351/203 |
| 9,280,910 B2 | * | 3/2016 | Baldwin | G09B 17/003 |
| 10,649,612 B2 | * | 5/2020 | Nelson | G06F 40/109 |
| 2006/0078858 A1 | * | 4/2006 | Vroman | A61B 5/16 434/179 |
| 2010/0253913 A1 | * | 10/2010 | Artal Soriano | A61B 3/032 351/223 |
| 2011/0299034 A1 | * | 12/2011 | Walsh | A61B 3/0091 351/206 |
| 2016/0027321 A1 | * | 1/2016 | Taylor | G09B 17/04 434/180 |
| 2016/0070105 A1 | * | 3/2016 | Tannoudiji | G02B 27/0172 345/8 |

(Continued)

*Primary Examiner* — Kurt Fernstrom
(74) *Attorney, Agent, or Firm* — Kim IP Law Group LLC

(57) ABSTRACT

Provided herein are devices, systems, methods, apparatuses, and computer program products for determining a visual acuity of a reader. The device includes a display adapted to present a first line of text to the reader and an input device adapted to receive signals corresponding to the first line of text. The device further includes a processor that is adapted to determine a reading score associated with the first line of text, generate an acuity parameter based on the reading score and the first readability vector, and determine the visual acuity of the reader based on the acuity parameter and a reference acuity parameter.

20 Claims, 4 Drawing Sheets

(56) References Cited

U.S. PATENT DOCUMENTS

| | | | |
|---|---|---|---|
| 2016/0198941 A1* | 7/2016 | Aguilar | G06T 7/11 |
| | | | 351/205 |
| 2017/0243507 A1* | 8/2017 | Ohme | G09B 7/06 |
| 2017/0358238 A1* | 12/2017 | Casutt | G06F 3/048 |
| 2018/0033329 A1* | 2/2018 | Suleiman | G09B 17/04 |
| 2019/0035300 A1* | 1/2019 | Bernstein | G09B 17/04 |
| 2020/0064657 A1* | 2/2020 | Hernandez Castaneda | |
| | | | A61B 3/028 |

* cited by examiner

VISUAL ACUITY MEASUREMENT APPARATUS

CROSS REFERENCE TO RELATED APPLICATIONS

This application claims priority under 35 U.S.C. § 119(e) to U.S. Provisional Patent Application No. 62/552,055, filed Aug. 30, 2017, entitled "Visual Acuity Measurement Apparatus," the disclosure of which is hereby incorporated by reference in its entirety.

BACKGROUND OF THE INVENTION

Conventional measurements of visual acuity are performed with a chart or card displaying a text passage that is presented to a reader. Measurements of visual acuity are made by, for example, timing the reader to determine how long the reader takes to complete reading several lines of text.

Such measurements are limited in that the lines of text or text passages on the chart or card are unchanging (that is, static). Consequently, such measurements require an administrator of a visual acuity test to provide a series of cards in order to characterize a reader's response to text passages with different characteristics. This limitation is particularly important when the visual acuity test is being performed in the context of medical treatment. Presenting a patient with multiple cards introduces delays to the testing process that decrease the effectiveness of the visual acuity measurement.

BRIEF SUMMARY OF THE INVENTION

To address the deficiencies of conventional measurements of visual acuity, in a first embodiment of the current disclosure, a device for determining a visual acuity of a reader is provided. The device includes a display adapted to present a first line of text to the reader and an input device adapted to receive signals corresponding to the first line of text. The device further includes a processor that is adapted to determine a reading score associated with the first line of text, generate an acuity parameter based on the reading score and the first readability vector, and determine the visual acuity of the reader based on the acuity parameter and a reference acuity parameter.

In another embodiment of the current disclosure, a computer program product for measuring visual acuity of a reader is provided. The computer program product includes a computer-readable non-transitory storage medium having computer-executable instructions stored thereon. The computer-executable instructions are executable to display a first line of text to the reader, the line of text being associated with a first readability vector. The computer-executable instructions are further executable to determine a first reading score associated with the first line of text and generate a first acuity parameter based on the first reading score and the first readability vector. Having generated a first acuity parameter, the computer-executable instructions are executable to generate a second acuity parameter by generating a second readability vector, which is made based on the first acuity parameter. The computer-executable instructions are further executable to display a second line of text, the second line of text associated with the second readability vector, and determine a second reading score associated with the second line of text. The second acuity parameter is generated based on the second reading score and the second readability vector. Finally, a determination is made of the visual acuity of the reader based on the first acuity parameter and the second acuity parameter.

In another embodiment of the present disclosure, a method for measuring visual acuity of a reader is provided herein. The method includes a step of displaying a line of text to the reader, where the line of text has an associated readability vector. The method further includes a step of determining a reading score associated with the line of text and generating an acuity parameter based on the reading score and the readability vector. The method also includes a step of determining the visual acuity of the reader based on the acuity parameter and a reference acuity parameter.

In yet another embodiment of the present disclosure, a software application (such as a mobile app) is provided for assessing visual acuity and reading speed. Such software may be employed to measure or determine the efficacy (that is, effectiveness) of a treatment designed to improve, e.g., patient health or the visual acuity and/or reading speed of the patient. Examples of such therapies may include, for example: delivery of a pharmaceutical treatment such as a drug to the patient, providing glasses to the patient, and/or providing contact lenses to a patient. Such software may be also employed to measure or determine a reading aptitude of the reader, or an employment fitness of the reader.

Currently such testing is performed manually by providing a patient with a reading card having static text (that is, the text is unmoving and unchanging). In order to evaluate the effectiveness of the therapy a test administrator records the amount of time required by a patient to read static text printed on the reading card. Typically, this time is recorded with a stopwatch.

In an exemplary embodiment of this disclosure a device is provided to a reader (who may be a patient in an example where the efficacy of a therapy is being evaluated by the device). The device includes a display on which a scrolling line of text dynamically appears. The scrolling of the text across the display occurs at a specified rate that is measured by the device. As the text scrolls across the display, the reader indicates his or her reading of the dynamic text by, for example, reading the text aloud to generate an audible signal corresponding to the words being read. The audible signal is received by a microphone that compares the words that are read to the displayed text, to collect data indicative of characteristics of the reader's reading such as: reading accuracy, visual acuity, and count of words read per minute, and/or speed of reading. Such data may be transmitted via a network interface to a central database for comparison with reference data (for example, reference acuity parameters). In addition, the scrolling text may vary dynamically the size of the font used to display the text, or other parameters such as a brightness or contrast used to display the text. By recording the font size, brightness, or contrast associated with the text on the screen and comparing the signal to the data indicative of the characteristics of the reader's reading, an acuity parameter may be generated, such as a reading index indicative of the number of words read per minute as a function of font size. In addition, the device can record an amount of time that the patient has spent reading the dynamic text, to generate a measurement of the acuity parameter as a function of time spent.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the subject disclosure, there are shown in the drawings exemplary embodiments. It should be understood, however, that the invention is not limited to the precise arrangements and instrumentalities shown.

In the drawings.

DETAILED DESCRIPTION OF THE INVENTION

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject disclosure in any matter not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the subject disclosure can be presented in a range format. It should be understood that the description in range format is merely for convenience and brevity and should not be construed as an inflexible limitation on the scope of the exemplary embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the exemplary embodiments can be practiced without one or more of the specific features or advantages of a particular embodiment. In other instances, additional features and advantages may be recognized in certain embodiments that may not be present in all exemplary embodiments of the subject disclosure.

Figure 1:
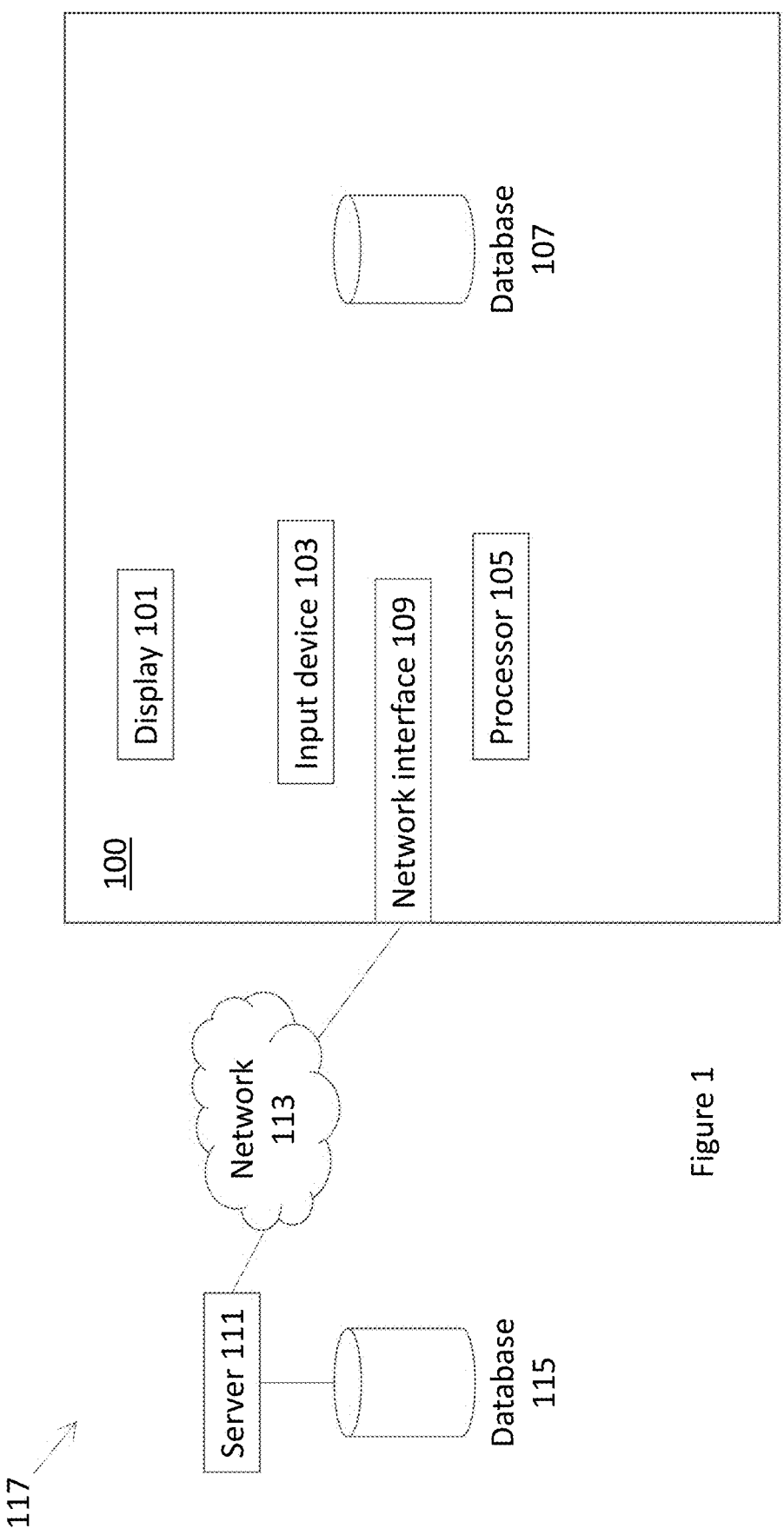
FIG. 1 is schematic diagram of a device in accordance with an exemplary embodiment.

FIG. 1 illustrates an exemplary system 117 for visual acuity measurement, in accordance with some embodiments. The system includes a device 100 in communication with a server 111 over a network 113. In an exemplary embodiment, the device presents text to a reader and receives information from the reader indicative of his or her reading of the text, in compliance with indicated reading tasks. The device may be, for example, a tablet computer, a smartphone, a personal digital assistant, a personal computer (PC) such as a desktop or laptop computer, or a headset with an integrated display such as a virtual reality headset of a PC. The computing device includes a display 101 that presents dynamic text passages to the reader. In exemplary embodiments, the display may be a greyscale display or may be a colored display and may allow variable contrast and colors between the text and the background. The device further includes an input device 103 that may include a joystick, a keyboard, a mouse, a microphone, a camera, or other similar tools suitable to receive input from a user. In certain exemplary embodiments, the input device may be used to record information indicative of the motion of the reader's eyes as the reader skims the dynamic text passage, e.g., the line of text. The input device allows the user to provide an input indicative of the dynamic text that the user is reading. In certain embodiments, the user may provide input indicative of the dynamic text that he or she is reading by typing in the displayed text via a keypad. In certain other embodiments, the user may provide input indicative of the dynamic text by reciting the text aloud as he or she reads so that a microphone may detect the audio.

The device 100 further includes a processor 105 for analyzing input from the reader and for recording timing of various events associated with the reader's reading. The processor is connected to the display 101 and adapted to provide signals to the display to control the dynamic presentation of the text. The processor is further adapted to receive input from the input device 103 and to process the input to determine characteristics of the reader's reading. The device is further connected to a database 107 and a network interface 109. The database includes information regarding reference information corresponding to text passages that are displayed (such as reference acuity parameters corresponding to the displayed text passages). Such reference information may be used by the processor in determining characteristics of the reader's reading.

The network interface 109 may be used to send information relating to the reader's reading over the network 113 to a central server 111. The central server may store the information, for example, in a central database 115. The central server may further process the received information to determine information relating to a reader's visual acuity or reading ability and store the reader's visual acuity measurements in the central database.

The network 113 may include one or more networks of the type commercially available in the marketplace or otherwise suitable for supporting communication between the device 100 and central server 111 in accord with the teachings herein. The network can be wired or wireless, a cellular network, a Local Area Network (LAN), a Wireless LAN (WLAN), a Metropolitan Area Network (MAN), a Wireless MAN (WMAN), a Wide Area Network (WAN), a Wireless WAN (WWAN), a Personal Area Network (PAN), a Wireless PAN (WPAN), or a network operating in accordance with existing IEEE 802.11, 802.11a, 802.11b, 802.11g, 802.11n, 802.11ac, 802.16, 802.16d, 802.16e, 802.16m standards or future versions or derivatives of such standards.

Figure 2:
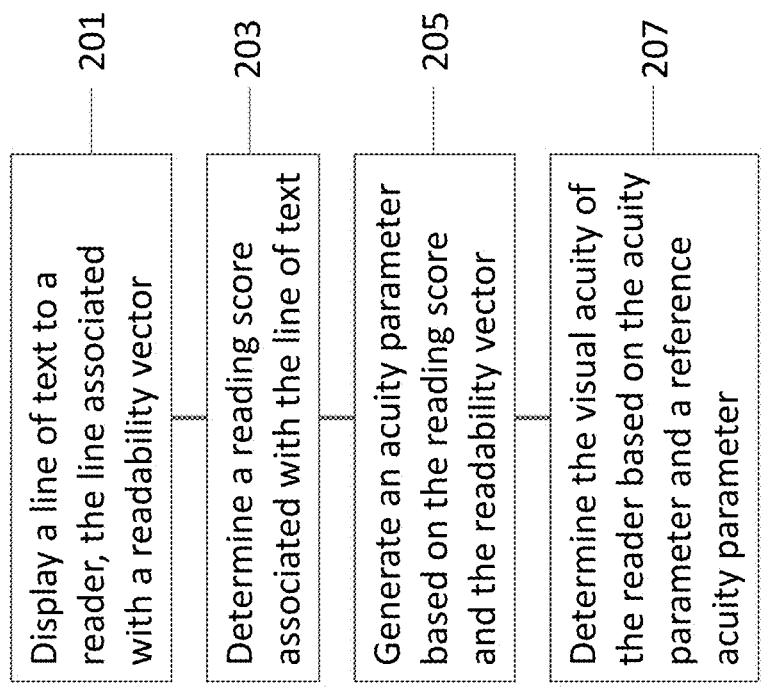
FIG. 2 shows a flow chart corresponding to a method in accordance with an exemplary embodiment.

FIG. 2 is a flow chart of an exemplary method of measuring visual acuity of a reader, in accordance with some embodiments. A computing device displays a line of text to the reader, where the line of text has an associated readability vector that includes certain parameters that determine how the display presents the text to the reader (step 201). In an embodiment, a readability vector includes parameters such as a font size, a font color, a background color, a display speed (e.g., a scroll speed), a brightness, and a contrast.

A reading score associated with the line of text is generated (step 203). Such a reading score may be generated, for example, by receiving input from the reader corresponding to the line of text that has been presented. Having received that input, the processor may generate a reading score based on the accuracy of the reading (that is, how well the received input corresponds to the line of text), the speed of the reading (that is, the amount of time between presentation of the line of text and the completion of the input indicating the reader's reading of the text).

In some embodiments, example input from the reader corresponding to the line of text that has been presented includes audio or keyboard input. For example, the reader may provide input indicative of the dynamic text that he or she is reading by typing in the displayed text via a keypad, a virtual keyboard, or a physical keyboard. Alternatively, the reader may recite the text aloud as he or she reads so that a microphone may detect the audio. Based on the received input, the processor may generate the reading score based on the accuracy of the reading. The processor may measure how well the received input corresponds to the line of text. For example, if the input is received via keypad, the processor may generate the reading score based on a number of correct or incorrect words compared with the displayed line of text. If the input is received via audio, the processor may determine a number of correct or incorrect words by converting the received audio into a set of phonemes and comparing the reader's phonemes to a reference phoneme set corresponding to the dynamic text. Such comparison may be performed by the processor on the reader's device as the reader is performing the indicated reading tasks. Alternatively, such comparison may be performed after the reader completes the indicated reading tasks, either by the processor on the reader's device or by providing the reader's phonemes to a central server that performs the comparison and transmits the result to the reader's device.

In further embodiments, if the input is received via audio, the processor may detect stops or interruptions in the reader's recited text. For example, the processor may identify a stop or interruption when the processor has not received or identified audio after a pre-configured time period, such as several seconds. Such stops or interruptions may indicate that the reader is having trouble with accuracy or speed of the dynamic text presented for the indicated reading tasks. Consequently, the present system may adjust the reading score of the reader downward to reflect detected stops or interruptions.

In some embodiments, the processor may determine the reading score based on the readability vector associated with the dynamic text. For example, the present system may vary a contrast or brightness of the displayed text, and determine the effect of such brightness or contrast variance on the accuracy and speed of the reader. In this way, the present system is able to measure a contrast sensitivity or a brightness sensitivity of the reader, and generate the reading score based on the contrast sensitivity or brightness sensitivity.

An acuity parameter is generated based on the reading score and the readability vector (step 205). The acuity parameter corresponds to the success of the reader in reading the line of text. By comparing the reader's acuity parameter to a reference acuity parameter, a visual acuity of the reader may be determined (step 207). Note that a reference acuity parameter typically corresponds to a particular readability parameter associated with text.

In certain exemplary embodiments, an assessment of the efficacy (that is, effectiveness) of a treatment such as a pharmaceutical product or an optical device (e.g., glasses or contact lenses) may be measured by periodic measurements of a visual acuity for a reader, such as before the treatment is provided and after the treatment is provided. In further embodiments, the assessment of the efficacy of the treatment can be based on an amount and/or duration of change in visual acuity measurements for the reader, such as changes in the reader's reading scores or acuity parameters.

In other embodiments, an assessment of a reading aptitude of the reader may be provided by measuring visual acuity for the reader. An individual reading aptitude index may be determined based on an individual visual acuity measurement. A method of assessing fitness of the reader as an employee candidate for a specified employment role may also be provided by measuring visual acuity for the reader. Alternatively, reading aptitude or employment fitness may be assessed over time based on analysis of periodic measurements of visual acuity.

In still other exemplary embodiments, a method of detecting changes in the reader's eye (that is, optical or ophthalmic changes) may be provided using periodic measurements of visual acuity for a reader. As a non-limiting example, the present visual acuity measurements can be used to detect a presence of changes in a retina of the reader. The macula is a region near the center of the retina that provides fine detail-oriented vision for a patient. Early detection of damage to the macula or retina, such as age-related macular degeneration (AMD), is desirable to provide a wide range of treatment options for the patient. For example, visual acuity data from periodic visual acuity measurements may be used for early detection of a presence of unwanted macula or retina changes. If the present system detects absolute or relative changes in periodic measurements of the patient's acuity parameters or reading scores, then the present system may trigger an alert, notification, or other indication suggesting that the patient seek ophthalmic or other medical treatment. Although AMD is described as one non-limiting example, the present visual acuity measurements may be used for early detection of retinal diseases such as diabetic retinopathy, lattice degeneration, epiretinal membrane or macular pucker, macular hole, central serous retinopathy, retinopathy of prematurity, uveitis, or other diseases of the retina and vitreous.

Detecting change in visual acuity measurements for the reader may be performed based on analysis of changes in absolute reading scores, absolute acuity parameters, relative reading scores, or relative acuity parameters. The changes may optionally be measured over specified durations of periodic visual acuity measurements. The periodic visual acuity measurements may be tracked for an individual reader, or based on data-driven analytic assessments such as analytics performed on big data sets that are aggregated and sampled from multiple readers. Periodic visual acuity measurements may be compared over specified periods of time such as days, weeks, months, or years.

Further embodiments of the present methods may perform statistical analysis on a set of visual acuity measurements to detect changes in visual acuity measurements. The present system may track change over time in a reader's visual acuity measurements, and trigger an alert, notification, or other indication if a decline or improvement in the visual acuity measurements is identified to be greater than a statistically significant amount. For example, the present system may track periodic average, mean, median, minimum, or maximum visual acuity measurements over time for a reader, and trigger an alert or notification if a subsequent visual acuity measurement declines or improves by an amount larger than a standard deviation or variance from a previous visual acuity measurement (or average, mean, or median thereof). The present system may also provide detection of potential optical or ophthalmic issues in a reader by identifying and comparing reference patterns of declines, such as patterns of declines determined from reference visual acuity measurements. The reference visual acuity measurements may be identified from patterns of decline in individual patients who are identified to be similar to the reader, or from aggregate patterns of decline in aggregate patient populations.

Some embodiments of the present visual acuity system may associate visual acuity scores with two- or three-dimensional images of the retina. Such images may be captured using, for example, optical coherence tomography (OCT) during a patient visit and timestamped with a date and time of the visit. The present system may identify a relevant time period associated with changes in a reader's visual acuity measurements. The present system may use the identified time period to suggest associated OCT images of the reader for review, for example, as a detection mechanism to determine whether medical treatment may be indicated as beneficial to the reader.

In some embodiments, the reader's eye movement may be tracked as the line of text scrolls dynamically across the display in order to generate an eye movement factor corresponding to the reader's response to a line of text with a particular readability vector. Such an eye movement factor may be incorporated into the measurement of the reader's visual acuity (e.g., the reader's acuity parameter or reading score) and may also be stored with the measurement of the reader's visual acuity to be incorporated into a diagnostic assessment of the reader's reading ability, visual acuity, and/or overall optical or ophthalmic health. The present system may generate the eye movement factor based on input received from the reader from the input device 103. For example, the present system may receive image or video data from the camera on the input device. The image data may be processed to detect the reader's pupil(s) or movement thereof, and generate an associated eye track number reflecting the detection of the reader's pupil(s) or the motion of the reader's eye(s).

In an embodiment, as described earlier, the system may receive from the user a first input indicative of dynamic text that the user is reading, such as audio or keyboard input relating to lines or passages of dynamic text. The present system may use the reader's eye movement factor as a second input indicative of the dynamic text that the reader is reading. For example, the system may use image or video input to detect the reader's pupils and confirm that the reader is looking at the displayed dynamic text and complying with indicated reading tasks. Accordingly, the system can generate the eye movement factor to measure the extent to which the reader is compliant with the indicated reading tasks from the system, based on the detected motion of the reader's eye and the reading speed of the reader.

Alternatively, the present system may track motion of the reader's eye to detect voluntary or involuntary eye movement. For example, the system may process image or video input from the input device's camera to detect voluntary or involuntary movement of the reader's pupils. Detected voluntary motion can provide a second input indicative of the dynamic text that the reader is reading, for example to confirm compliance with indicated reading tasks from the system. Detected involuntary motion can provide an input into the reader's visual acuity measurements, including the generated eye track number, eye movement factor, the reading speed, the reading score, or the acuity parameter of the reader. For example, the present system can detect involuntary motion by processing groups of images or sequential image frames from image or video input received from the input device's camera, to detect and compare the reader's pupils across image groups or frames. A nystagmus refers to an ophthalmic condition in which a patient's eyes make repetitive, involuntary movements that can result in reduced vision. These involuntary movements can occur from side to side (horizontal nystagmus), up and down (vertical nystagmus), or in a circular pattern (rotational nystagmus). The present system may generate an eye movement factor to account for a determination that a reader has a nystagmus, and update the reader's reading score or acuity parameter based on the generated eye movement factor. Accordingly, the system can generate the eye movement factor to measure the reader's compliance with indicated reading tasks or to detect clinically relevant eye motion that could affect indicated reading tasks, based on the detected motion of the reader's eye and the reading speed of the reader.

In various embodiments, the method steps described herein, including the method steps described in FIG. 2 may be performed in an order different from the particular order described or shown. In other embodiments, other steps may be provided, or steps may be eliminated, from the described methods.

Figure 3:
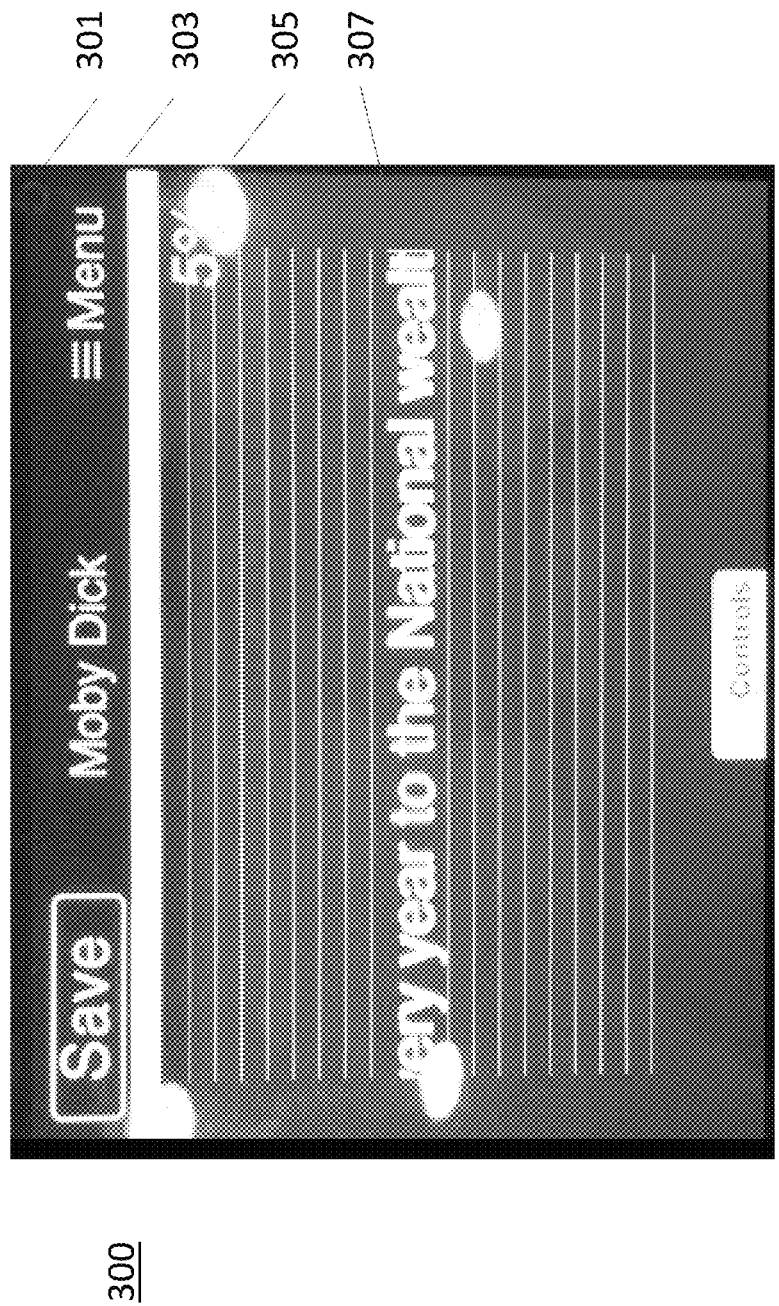
FIG. 3 shows a device for displaying a line of scrolling text in accordance with an exemplary embodiment.

FIG. 3 shows an example tablet device 300 in accordance with an embodiment. The device includes a display 301, an input menu 303 suitable to receive user input via a touch screen, a background 305, and a line of text 307.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. For example, in an exemplary embodiment, processor 105 may act as a client with respect to a server 111 that may act as a server with respect to other networked devices. Typically, in such a system 117, the client computers are located remotely from the server computer and interact via a network 113. The client-server relationship may be defined and controlled by computer programs running on the respective client and server computers.

Systems, apparatus, and methods described herein may be used within a network-based cloud computing system. In such a network-based cloud computing system, a server 111 or another processor that is connected to a network 113 communicates with one or more client computers 100 via the network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIG. 2. Alternatively, for example, the client or clients may transmit a request adapted to cause a server computer or computers to perform one or more of the method steps described herein, including one or more of the steps of FIG. 2. Certain steps of the methods described herein, including one or more of the steps of FIG. 2, may be performed by a server or by another processor in a network-based cloud-computing system. Certain steps of the methods described herein, including one or more of the steps of FIG. 2, may be performed by a client computer in a network-based cloud computing system. The steps of the methods described herein, including one or more of the steps of FIG. 2, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 2, may be implemented using one or more computer programs that are executable by such a processor. A computer program is a set of computer program instructions that may be used, directly or indirectly, in a computer to perform a certain activity or bring about a certain result. A computer program may be written in any form of programming language, including compiled or interpreted languages, and it may be deployed in any form, including as a stand-alone program or as a module, component, subroutine, or other unit suitable for use in a computing environment.

Figure 4:
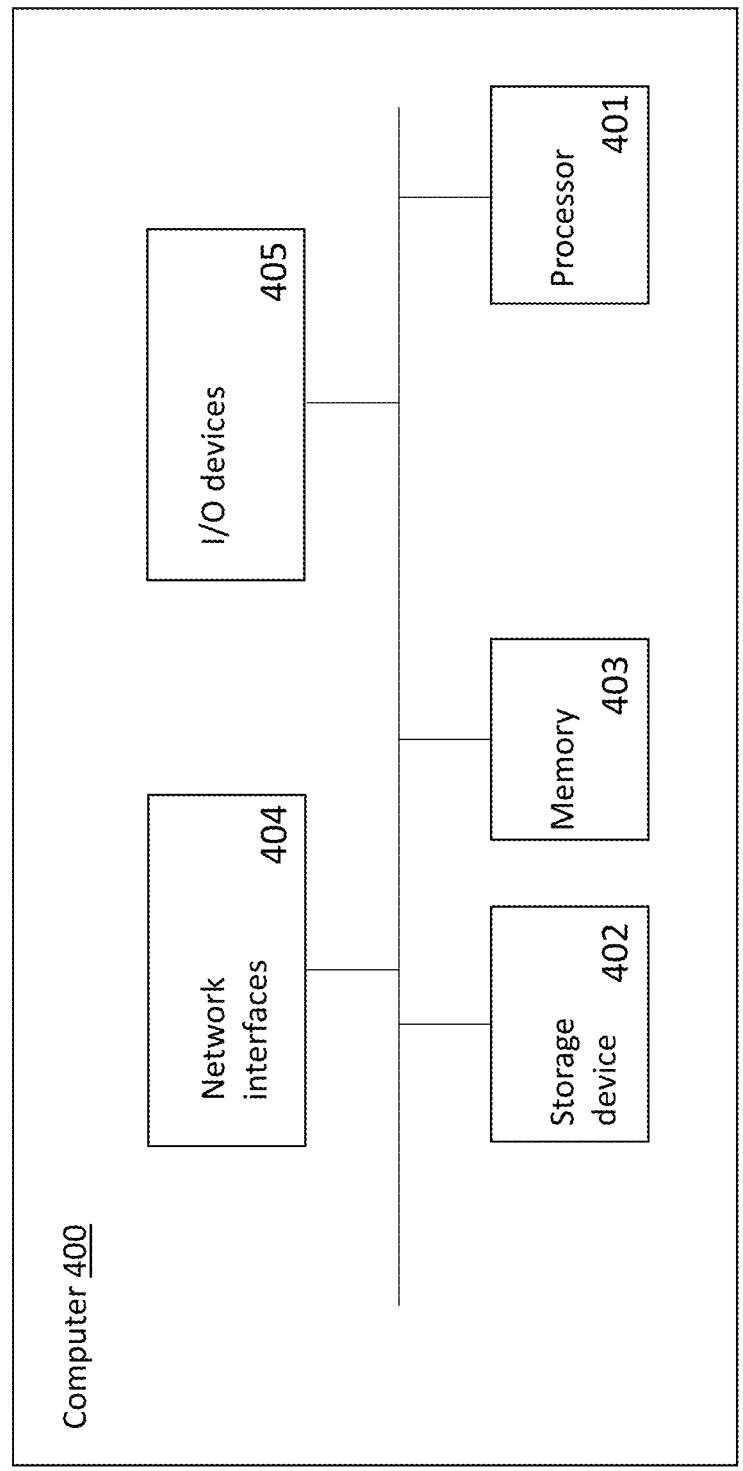
FIG. 4 shows components of an exemplary computer that may be used to implement the system as described herein in accordance with an exemplary embodiment.

A high-level block diagram of an exemplary computer that may be used to implement systems, apparatus and methods described herein is illustrated in FIG. 4. Computer 400 comprises a processor 401 operatively coupled to a data storage device 402 and a memory 403. Processor 401 controls the overall operation of computer 400 by executing computer program instructions that define such operations. The computer program instructions may be stored in data storage device 402, or other computer-readable medium, and loaded into memory 403 when execution of the computer program instructions is desired. Thus, the method steps of FIG. 2 may be defined by the computer program instructions stored in memory 403 and/or data storage device 402 and controlled by the processor 401 executing the computer program instructions. For example, the computer program instructions may be implemented as computer executable code programmed by one skilled in the art to perform an algorithm defined by the method steps of FIG. 2. Accordingly, by executing the computer program instructions, the processor 401 executes an algorithm defined by the method steps of FIG. 2. Computer 400 also includes one or more network interfaces 404 for communicating with other devices via a network. Computer 400 also includes one or more input/output devices 405 that enable user interaction with computer 400 (e.g., display, keyboard, mouse, speakers, microphone, camera, buttons, etc.).

Processor 401 may include both general and special purpose microprocessors, and may be the sole processor or one of multiple processors of computer 400. Processor 401 may comprise one or more central processing units (CPUs), for example. Processor 401, data storage device 402, and/or memory 403 may include, be supplemented by, or incorporated in, one or more application-specific integrated circuits (ASICs) and/or one or more field programmable gate arrays (FPGAs).

Data storage device 402 and memory 403 each comprise a tangible non-transitory computer-readable storage medium. Data storage device 402, and memory 403, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 405 may further include peripherals, such as a printer, scanner, display screen, etc. For example, input/output devices 405 may include a display device such as a cathode ray tube (CRT) or liquid crystal display (LCD) monitor for displaying information to the user, a keyboard, and a pointing device such as a mouse or a trackball by which the user can provide input to computer 400.

Any or all of the systems and apparatus discussed herein, including parts such as system 117, device 100, server 111, or processor 105 and components thereof, may be implemented using a computer such as computer 400.

One skilled in the art will recognize that an implementation of an actual computer or computer system may have other structures and may contain other components as well, and that FIG. 4 is a high level representation of some of the components of such a computer for illustrative purposes.

While the subject disclosure has been described with reference to exemplary embodiments, it will be appreciated by those skilled in the art that various changes may be made and equivalents may be substituted for elements thereof without departing from the scope of the subject disclosure. For example, additional components and steps can be added to the devices and the various visual acuity measurement methods. In addition, modifications may be made to adapt a particular situation or material to the teachings of the exemplary embodiments without departing from the essential scope thereof. It is to be understood, therefore, that the exemplary embodiments not be limited to the particular aspects disclosed, but it is intended to cover modifications within the spirit and scope of the subject disclosure as defined by the appended claims.

I claim:

1. A device for determining a visual acuity of a reader, the device comprising:

a display adapted to present a scrolling first line of text to a reader, the scrolling first line of text having an associated first readability vector including an associated scrolling speed and an associated font size;

an input device adapted to receive signals reflecting a reading performance of the reader when reading the scrolling first line of text; and a processor communicatively coupled to the input device and configured to:

determine a reading score for the reader associated with the scrolling first line of text based on the received signals from the input device and on the associated scrolling speed;

generate an acuity parameter for the reader, wherein the acuity parameter comprises a reading index determined based on the reading score and the associated font size; and determine a visual acuity of the reader based on the acuity parameter relative to a reference acuity parameter.

2. The device of claim 1, wherein the readability vector further comprises at least one of a font color, a background color, a brightness, and a contrast.

3. The device of claim 1, wherein the processor configured to determine the reading score comprises the processor being configured to determine a reading speed of the reader based on the received signals from the input device and on the associated scrolling speed.

4. The device of claim 1, wherein the processor is further configured to determine an effectiveness of a treatment, a reading aptitude of the reader, or an employment fitness of the reader based on the visual acuity.

5. The device of claim 1, wherein the processor is further configured to detect changes in the reader's eye based on the visual acuity, the changes including at least one of age-related macular degeneration, diabetic retinopathy, lattice degeneration, epiretinal membrane or macular pucker, macular hole, central serous retinopathy, retinopathy of prematurity, and uveitis.

6. The device of claim 1, wherein the input device comprises a microphone that generates an audio signal based on receiving audio corresponding to the reader reading aloud the scrolling first line of text, and wherein the processor is further configured to:

determine the reading score for the reader by determining a reading speed for the reader based on the audio signal received from the microphone and on the associated scrolling speed.

7. The device of claim 6, wherein the input device further comprises a camera that generates an image or video signal including an image or video corresponding to the reader's eye, and wherein the processor is further configured to:

generate an eye track number based on a measurement of the reader's eye movement while the reader is reading aloud the scrolling line of text, wherein the measurement of the reader's eye movement is determined based on the image or video signal received from the camera, and generate an eye movement factor based on the eye track number and the reading speed.

8. A computer program product for measuring visual acuity of a reader, comprising a computer-readable non-transitory storage medium having computer-executable instructions stored thereon, the computer-executable instructions executable to perform:

displaying a scrolling first line of text to a reader, the scrolling first line of text having an associated first readability vector including an associated first scrolling speed and an associated first font size;

receiving first signals from an input device wherein the received first signals reflect a first reading performance of the reader when reading the scrolling first line of text;

determining a first reading score for the reader associated with the scrolling first line of text based on the received first signals from the input device and on the associated first scrolling speed;

generating a first acuity parameter for the reader, wherein the acuity parameter comprises a first reading index determined based on the first reading score and the associated first font size;

generating a second readability vector based on the first acuity parameter;

displaying a scrolling second line of text, the scrolling second line of text associated with the second readability vector including an associated second scrolling speed and an associated second font size;

receiving second signals from the input device wherein the received second signals reflect a second reading performance of the reader when reading the scrolling second line of text;

determining a second reading score for the reader associated with the scrolling second line of text based on the received second signals from the input device and on the associated second scrolling speed;

generating a second acuity parameter for the reader, wherein the second acuity parameter comprises a second reading index determined based on the second reading score and the associated second font size; and determining a visual acuity of the reader based on the first acuity parameter and the second acuity parameter.

9. The computer program product of claim 8, wherein the first readability vector further comprises at least one of a font color, a background color, a display speed, a brightness, and a contrast.

10. The computer program product of claim 8, wherein the computer-executable instructions executable to determine the first reading score for the reader comprise the computer-executable instructions being executable to determine a first reading speed of the reader based on the received first signals from the input device and on the associated first scrolling speed.

11. The computer program product of claim 8, wherein the computer-executable instructions are executable to further perform: determining an effectiveness of a treatment, a reading aptitude of the reader, or an employment fitness of the reader based on the first and second acuity parameters.

12. The computer program product of claim 8, wherein the computer-executable instructions are executable to further perform: detecting changes in the reader's eye based on the first and second acuity parameters, the changes including at least one of age-related macular degeneration, diabetic retinopathy, lattice degeneration, epiretinal membrane or macular pucker, macular hole, central serous retinopathy, retinopathy of prematurity, and uveitis.

13. The computer program product of claim 8, wherein the input device comprises a microphone; and wherein the computer-executable instructions executable to determine the first reading score for the reader include computer-executable instructions executable to perform: determining a first reading speed of the reader based on receiving, using the microphone, audio corresponding to the reader reading aloud the scrolling first line of text.

14. The computer program product of claim 13,
wherein the input device further comprises a camera; and
wherein the computer-executable instructions are executable to further perform:
- tracking, using the camera, a motion of the reader's eye while the reader is reading aloud the scrolling first line of text, and
- generating an eye movement factor based on the motion of the reader's eye and the reading speed.

15. A computer-implemented method for measuring visual acuity of a reader, the method comprising:
- displaying, on a display operatively coupled to a computer, a scrolling line of text to a reader, the scrolling line of text having an associated readability vector including an associated scrolling speed and an associated font size;
- receiving, from an input device communicatively coupled to the computer, signals reflecting a reading performance of the reader when reading the scrolling line of text determining, using the computer, a reading score for the reader associated with the scrolling line of text based on the received signals from the input device and on the associated scrolling speed;
- generating, using the computer, an acuity parameter for the reader, wherein the acuity parameter comprises a reading index determined based on the reading score and the associated font size; and
- determining, using the computer, a visual acuity of the reader based on the acuity parameter relative to a reference acuity parameter.

16. The method of claim 15, wherein the readability vector further comprises at least one of a font size, a font color, a background color, a brightness, and a contrast.

17. The method of claim 15, wherein the step of determining the reading score comprises determining a reading speed of the reader based on the received signals from the input device and on the associated scrolling speed.

18. The method of claim 15, further comprising determining an effectiveness of a treatment, a reading aptitude of the reader, or an employment fitness of the reader based on the visual acuity.

19. The method of claim 15, further comprising detecting changes in the reader's eye based on the visual acuity, the changes including at least one of age-related macular degeneration, diabetic retinopathy, lattice degeneration, epiretinal membrane or macular pucker, macular hole, central serous retinopathy, retinopathy of prematurity, and uveitis.

20. The method of claim 15,
wherein the input device comprises a microphone communicatively coupled to the computer; and
wherein the step of determining the reading score for the reader further comprises determining a reading speed of the reader-based on receiving, from the microphone, audio generated by the reader corresponding to the reader reading aloud the scrolling line of text.

* * * * *